(12) United States Patent
Bonnet et al.

(10) Patent No.: US 9,146,237 B2
(45) Date of Patent: Sep. 29, 2015

(54) IN VITRO ASSAY METHOD USING IMMUNOLOGICAL TECHNIQUE

(75) Inventors: Sébastien Bonnet, Saint Jean de Niost (FR); Delphine Rival, Ternay (FR)

(73) Assignee: BASF Beauty Care Solutions France S.A.S., Lyons (FR)

(*) Notice: Subject to any disclaimer, the term of this patent is extended or adjusted under 35 U.S.C. 154(b) by 0 days.

(21) Appl. No.: 14/127,317

(22) PCT Filed: Jun. 18, 2012

(86) PCT No.: PCT/EP2012/061603
§ 371 (c)(1),
(2), (4) Date: Feb. 14, 2014

(87) PCT Pub. No.: WO2012/175454
PCT Pub. Date: Dec. 27, 2012

(65) Prior Publication Data
US 2014/0162284 A1    Jun. 12, 2014

(30) Foreign Application Priority Data
Jun. 20, 2011 (FR) ...................................... 11 55415

(51) Int. Cl.
*G01N 33/53* (2006.01)
*G01N 33/569* (2006.01)
*G01N 33/50* (2006.01)

(52) U.S. Cl.
CPC ...... *G01N 33/56966* (2013.01); *G01N 33/5023* (2013.01); *G01N 2333/4753* (2013.01); *G01N 2333/49* (2013.01); *G01N 2333/50* (2013.01); *G01N 2333/78* (2013.01)

(58) Field of Classification Search
None
See application file for complete search history.

(56) References Cited

U.S. PATENT DOCUMENTS

| 5,420,016 A * | 5/1995 | Boguslaski et al. ............ 435/12 |
| 5,543,332 A * | 8/1996 | Lihme et al. .................. 436/528 |
| 5,902,741 A * | 5/1999 | Purchio et al. ................ 435/325 |
| 2006/0024723 A1 * | 2/2006 | Hussa et al. ...................... 435/6 |
| 2006/0079439 A1 | 4/2006 | Li et al. |
| 2009/0104201 A1 | 4/2009 | Smith et al. |
| 2012/0263680 A1 * | 10/2012 | Lander et al. ................ 424/85.5 |

FOREIGN PATENT DOCUMENTS

| EP | 0 387 777 A2 | 9/1990 |
| GB | 2 438 999 A | 12/2007 |
| WO | WO-03/062830 A2 | 7/2003 |
| WO | WO-2009/121422 A1 | 10/2009 |

OTHER PUBLICATIONS

Diquélou, A., et al., "Relationship between Endothelial Tissue Factor and Thrombogenesis under Blood Flow Conditions", Thrombosis and Haemostasis, 1995, vol. 74, No. 2, pp. 778-783.
Ryan, J., et al., Tumor Necrosis Factor-Induced Endothelial Tissue Factor Is Associated with Subendothelial Matrix Vesicles but Is not Expressed on the Apical Surface, Blood, 1992, vol. 80, No. 4, pp. 966-974.
Dooley, A., et al., "Modulation of Collagen Type 1, Fibronectin and Dermal Fibroblast Function and Activity, in Systemic Sclerosis by the Antioxidant Epigallocatechin-3-Gallate", Rheumatology, 2010, vol. 49, pp. 2024-2036.
Dooley, A., et al., "Effect of Nitric Oxide and Peroxynitrite on Type I Collagen Synthesis in Normal and Scleroderma Dermal Fibroblasts", Free Radical Biology & Medicine, 2007, vol. 43, pp. 253-264.
International Search Report for PCT/EP2012/061603 mailed Mar. 27, 2013.
Office Communication Issued in European Patent Application No. 12730871.6 Dated Jun. 18, 2015, English portions only.

* cited by examiner

*Primary Examiner* — Gary W Counts
(74) *Attorney, Agent, or Firm* — Drinker Biddle & Reath LLP

(57) ABSTRACT

The present application relates to a novel method of in vitro assay of the molecules of the extracellular matrix synthesized by cells in culture and uses thereof in the form of a kit for in vitro measurement and/or for a method of screening of cosmetic and/or pharmaceutical ingredients.

22 Claims, No Drawings

IN VITRO ASSAY METHOD USING IMMUNOLOGICAL TECHNIQUE

RELATED APPLICATIONS

This application is a national stage application (under 35 U.S.C. §371) of PCT/EP2012/061603, filed Jun. 18, 2012, which claims benefit of French Application No. 1155415, filed Jun. 20, 2011.

The present invention relates to a novel method of in vitro assay of the molecules of the extracellular matrix synthesized by cells in culture and uses thereof as a kit for measurement in vitro and/or as a method of screening cosmetic and/or pharmaceutical ingredients.

The extracellular matrix (ECM) performs an essential role in the structure of the tissues of the body of humans and animals, in particular by its functions of support, adherence and regulation of cellular exchanges. The ECM is largely constituted of glycoproteins, proteins and glycosaminoglycans. These molecules are synthesized in native form in the cells in contact with the ECM. From the intracellular compartment, they are excreted outside of the cells. After phenomena of maturation, they become organized and arranged as a network, which forms the ECM. They are then in their functional form.

The molecules of the ECM are the subject of research particularly in the cosmetic and pharmaceutical fields, where numerous ingredients aim to stimulate their synthesis and thus improve the general state of the tissue in question.

In vitro, cells in culture in suitable conditions produce their extracellular matrix and constitute a particularly simple model for studies, notably for measuring the activity of synthesis, by the cells, of one or more molecules constituting the ECM and the influence of ingredients on this activity. In this type of model of cells in culture, the molecules of the ECM are present, optionally in various forms, notably as precursors, in different culture compartments: intracellular compartment, in the culture medium compartment, or are contained in the ECM compartment.

The classical measurement techniques consist of measuring the quantity of molecules of the ECM in the culture medium. Thus, according to the commonest technique, the ELISA technique is used for assaying molecules of the ECM such as collagens in the culture medium, optionally in their precursor form such as procollagen. Another technique that is more expensive, more restrictive and of more general application, consists of including, in the culture medium, radiolabelled molecules used by the cells for synthesis of the molecules of the ECM, and of overall measurement of the intensity of the radioactivity thus obtained in all of the compartments. For example, tritiated proline is used for measuring the overall amount of collagen produced by the cells in culture. These techniques are able to show the activity of synthesis of the cells in culture but not the functionality of the molecules thus synthesized, i.e. of the quantity of molecules in the ECM.

Only immunohistochemical analysis makes it possible to determine, and only partly, the functionality of the molecules of the ECM thus synthesized. This technique consists of removing the culture medium, labelling with antibodies directed against the molecules of the ECM under investigation, then reading and/or visualizing the fluorescence. This technique makes it possible to quantify the molecules contained in the intracellular compartment, extracellular compartment and in the ECM and especially to visualize their localization. However, this technique is difficult to implement and requires expensive equipment. Moreover, the technique in itself does not allow a large number of ingredients to be analysed. Furthermore, it is subjective and depends on the experimenter. Thus, before the present invention, no objective quantitative measurement allowed determination of the quantity of functional molecules, i.e. molecules really incorporated into the ECM and notably molecules constituting the ECM, in a sufficiently quick, reliable, simple and predictive manner. Moreover, no method allowed the screening of ingredients of cosmetic and/or pharmaceutical interest.

However, a high level of synthesis of molecules of the ECM by cells in culture measured in the intracellular compartment and/or in the extracellular compartment does not necessarily result in a larger amount of functional molecules, i.e. of molecules in the ECM.

Indeed, the applicant was able to show that certain cosmetic active ingredients can provide overall stimulation of the synthesis of collagen of the ECM but without observing improvement of collagen functionality, i.e. no increase in the content of collagen in the ECM. The applicant also found that certain ingredients improve collagen functionality, i.e. its content in the ECM but without measuring an increase in the synthesis of procollagen (examples 6 and 7).

The techniques of the prior art are therefore unsuitable for quantifying the functionality of the molecules of the ECM, i.e. their content in the ECM, in that they are not direct and are not sufficiently reliable, predictive, reproducible, repeatable and specific. Moreover, they do not permit screening of cosmetic and/or pharmaceutical ingredients that potentially improve the functionality of the molecules of the ECM in a satisfactory manner or make it possible to visualize their effects in the ECM.

Publications Diquélou A. et al, 1995, Relationship between endothelial tissue factor and thrombogenesis under blood conditions, Thrombosis and haemostasis, vol 74, n° 2, p 778-783 and Ryan J et al, 1992, Tumor necrosis factor-induced endothelial tissue factor is associated with subendothelial matrix vesicles but is not expressed on the apical surface, Blood, vol 80, n° 4, p 966-974, described the assaying of TF synthesized by HUVECS after 4 or 8 hours of culturing. However, such culture times are too short to allow synthesis of ECM by cells in culture and to study functionality of molecules constituting and/or contained in the ECM. These experiments have indeed another purpose.

There was therefore a need for a technique for assaying molecules of the ECM synthesized by cells in culture by which the functionality of the molecules of the ECM, i.e. their content in the ECM, can be assayed directly and quantitatively, in a reliable, simple, repeatable, predictive and specific manner. There was, moreover, a need for a technique which does not degrade the ECM and makes it possible to visualize and quantify the molecule studied within the ECM and to study it, in situ, in particular in its functional form and to study its interactions with the other molecules of the ECM.

The applicant recently discovered, surprisingly and unexpectedly, that this problem can be solved by carrying out a specific step of lysis of cells in culture and of assaying the molecules of interest directly on the ECM. The method according to the invention thus provides a technical solution to the problem of the prior art and has the advantage of being rapid, suitable for miniaturization, and of permitting the screening of a large number of ingredients for their capacity for increasing or decreasing the quantity of molecules in the ECM, advantageously in a form that can be automated. The method according to the invention also has the advantage of not destroying the ECM and making it possible to both quantify and visualize the molecules of the ECM.

The present invention relates to a method of in vitro assay method using an immunological technique of at least one molecule of the extracellular matrix synthesized by cells in culture comprising at least the steps:
a) a step of culturing the cells and preferably culturing the cells at confluency for at least 24 hours,
b) a preferred step of collecting the culture medium,
c) a step of cell lysis with a solution of quaternary amine, preferably at a concentration in the range from 100 μM to 2 M,
d) a step of collecting the cell lysate,
e) a step of assaying said molecule in the extracellular matrix by an immunological technique.

The present invention also relates to a method of in vitro assay method using an immunological technique of at least one molecule of the extracellular matrix synthesized by cells in culture comprising at least the steps:
a) a step of cell culturing the cells, and preferably culturing the cells at confluency for at least 24 hours,
b) a step of collecting the culture medium and of assaying the molecule of the ECM and/or a precursor of the molecule of the ECM,
c) a step of cell lysis with a solution of quaternary amine, preferably at a concentration in the range from 100 μM to 2 M,
d) a step of collecting the cell lysate and of assaying the DNA and/or of assaying the molecule of the ECM and/or a precursor of the molecule of the ECM,
e) a step of assaying said molecule of the ECM contained in the extracellular matrix by an immunological technique.

The present invention also relates to the use of the assay method according to the invention for screening and/or in vitro study of at least one ingredient of cosmetic and/or pharmaceutical interest for its properties of increasing or decreasing the quantity of a molecule in the extracellular matrix.

The present invention also relates to a method of screening and/or of in vitro study of at least one ingredient of cosmetic and/or pharmaceutical interest for its properties of increasing or decreasing the quantity of a molecule in the extracellular matrix comprising at least the steps:
a) a step of culturing the cells in the presence of the ingredient and preferably culturing the cells at confluency for at least 24 hours in the presence of the ingredient,
b) preferably a step of collecting the culture medium and more preferably of assaying the molecule of the ECM and/or a precursor of the molecule of the ECM in said culture medium thus collected,
c) a step of cell lysis with a solution of quaternary amine, preferably at a concentration in the range from 100 μM to 2 M,
d) a step of collecting the cell lysate and preferably of assaying the DNA and/or of assaying the molecule of the ECM and/or a precursor of the molecule of the ECM,
e) a step of assaying said molecule of the ECM contained in the extracellular matrix by an immunological technique.

The present invention also relates to a kit for assay by an immunological method, useful according to one of the methods according to the invention, comprising at least one solution of quaternary amine, preferably at a concentration in the range from 100 μM to 2M, and an antibody directed against the molecule of the ECM, optionally bound to a secondary antibody.

The present invention also relates to a method of selection of a lysis solution useful in the assay method according to the invention, wherein the assay method according to the invention is carried out with a lysis solution to be tested for at least 10 min, preferably 10 min, and the ratio of the result of the assay of the molecule of the ECM obtained in step e) to the result of the assay of the DNA in the cell lysate is compared with that obtained with an ammonium hydroxide lysis solution at 20 mM applied for the same time, preferably 10 minutes.

According to the invention, "molecules of the ECM" means the organic molecules that constitute and/or are contained in the extracellular matrix and are synthesized by cells, of human or animal origin.

These are notably proteins constituting the ECM, in particular selected from:
The family of collagens of the ECM: the fibrillar collagens notably type I, III or V collagens, the FACITS collagens (Fibril Associated Collagen with Interrupted Triple Helix) notably type VI, XII, XIV or XVI collagens, collagens IV and VII, collagens XXII, XXVII, XVIII
The family of elastic fibers of the ECM: elastin, tropoelastin, proteins associated with elastin notably fibrillin 1, lysyl oxidases, notably LOX and LOXL, EBP (Elastin Binding Protein), fibulins 3 and 5, Emilin 1 and 2.

These are notably proteoglycans constituting the ECM, in particular secreted proteoglycans selected from perlecan, versican, leucine-rich proteoglycans (SLRPs) notably decorin, biglycan and lumican.

They are also glycoproteins constituting the ECM, notably fibronectin, laminin, SPARC (Secreted Protein Rich in Cysteine), tenascin, nidogen-1.

They are moreover glycosaminoglycans (GAG) constituting the ECM, in particular hyaluronic acid, heparan sulfate, dermatan sulfate, chondroitin sulfate.

They are also growth factors of the ECM which are proteins contained in the ECM, notably VEGF, PDGF, HGF, the FGFs, and in particular FGF2 and FGF7.

The present invention very advantageously makes it possible to assay and study molecules constituting the ECM and to visualize them in situ in the well, that is to say without destroying the ECM.

Certain molecules of the ECM are present in compartments other than the ECM in a precursor form.

The "molecules of the ECM" means molecules in the ECM or in other compartments notably intracellular compartment and extracellular compartment in the culture medium, optionally in precursor forms.

According to the invention, "precursor of the molecule of the ECM" means a native and/or intermediate form of the molecule of the ECM, synthesized by the cell, before constituting or being contained in the ECM. These forms undergo phenomena of maturation before being in the ECM and are thus often denoted by the prefixes "Pro-" or "Tropo-". They are for example procollagens, tropocollagens, proelastin, tropoelastin.

According to the invention, "cells in culture" means the human or animal cells capable of synthesizing one or more molecules of the ECM. In the method according to the present invention, these cells in culture are cultured and one or several molecules of the ECM that have been synthesized by these cells are assayed according to the present invention. These cells are preferably of differentiated type, and in particular can be differentiated precursor type cells or differentiated non-precursor type cells or a mix thereof. They can be normal, mutated or immortalized, cultured in monolayer optionally in coculture with one or more other cell types capable or not of synthesizing one or more molecules of the ECM. These cells are notably stromal cells, preferably fibroblasts, osteoblasts and/or adipoblasts, preadipocytes, adipocytes, epithelial cells, preferably keratinocytes or endothelial cells. They are extracted from biopsies, preferably from skin biopsies, or are in cell lines. According to a preferred embodiment, the present invention is quite particularly advantageous for studying molecules constituting the ECM and synthesized by fibroblasts in culture. Indeed, a functional ECM is essential in the structure of cutaneous tissues and the method according to the present invention provides access in the culture well, including after 2 to 4 days culturing fibroblasts post-confluence.

According to the invention, "immunological method" means the techniques of quantitative assay using antibodies directed against proteins or sugars.

They are enzyme-substrate assay techniques of EIA (Enzyme Immuno Assay) type, notably ELISA (Enzyme-Linked Immunosorbent Assay), RIA (radioimmunoassay) radiolabelling, and fluorescence measurement called FIA (Fluorescent immunoassay), in particular by time-delayed fluorescence, called TRF (Time Resolved Fluorescence).

According to the invention, "ingredient of cosmetic and/or pharmaceutical interest" means one or more natural and/or synthetic molecules, and/or a vegetable extract, optionally synthesized and/or modified by biological engineering, in particular by fermentation by microorganisms, of which the properties on the molecules of the ECM are evaluated for its capacities for increasing or decreasing the quantity of the molecule in the ECM.

The object according to the invention is a method of in vitro assay method using an immunological technique of at least one molecule of the extracellular matrix synthesized by cells in culture comprising at least the successive steps:
  step of culturing the cells,
  a preferred step of collecting the culture medium,
  step of cell lysis with a solution of quaternary amine,
  step of collecting the cell lysate,
  step of assaying said molecule contained in the extracellular matrix by an immunological technique.

The method according to the invention makes it possible to assay at least one molecule of the ECM and advantageously one or two, more preferably at least two.

According to a preferred embodiment, the molecules of the ECM are selected from the proteins constituting the ECM, the glycoproteins constituting the ECM, the glycosaminoglycans constituting the ECM, the proteoglycans constituting the ECM and the growth factors contained in the ECM. More preferably, they are selected from type I, III, V, VI, XII, XIV, XVI, IV and VII collagens, elastin, tropoelastin, fibrillin 1, LOX, LOXL, EBP (Elastin Binding Protein), fibulins 3 and 5, Emilin 1 and 2, perlecan, versican, decorin, biglycan, lumican, fibronectin, laminin, hyaluronic acid, heparan sulphate, VEGF, PDGF, FGF-2, FGF-7, and HGF.

According to a particularly advantageous embodiment, the molecules of the ECM are selected from type I, III, V, XVIII, IV and VII collagens, perlecan, fibronectin, FGF-2, elastin, hyaluronic acid. According to a preferred embodiment, the molecules of the ECM are selected from type I, III, V, XVIII, IV and VII collagens.

The cells capable of synthesizing the molecules of the ECM are cultured in vitro preferably in monolayer according to the usual techniques in this area. They are seeded on a suitable culture substrate, preferably a cell culture plate comprising wells, and cultured in a suitable culture medium up to confluency, preferably between 80 and 100% of confluency, more preferably between 90 and 100%, more preferably 100%.

For use of the method in medium-throughput screening, the plates are advantageously 96-well or 384-well plates. These plates can conventionally be coated, that is to say treated, with a specific coating to improve cells adhesion. Such coating can be molecules constituting the ECM. Preferably, the plates are uncoated or coated with a molecule which is not the same as the molecule which is assayed and/or of which the content in the ECM is studied.

According to a preferred embodiment, the cells in culture are selected from fibroblasts, preferably dermal fibroblasts and/or keratinocytes and/or adipocytes, are advantageously human cells, and are preferably extracted from biopsies, preferably from skin biopsies, and are preferably normal human cells, i.e. not mutated and not immortalized cells. Indeed, the studies undertaken have shown that the method according to the invention is particularly suitable for these cell types.

It is generally at confluency that the cells will begin to secrete the molecules of the ECM. Thus, advantageously, the cells are maintained in culture at confluency for a length of time of at least 24 hours and preferably up to 6 days, preferably in the range from 24 to 96 hours, and more preferably for 48 hours. According to a particularly advantageous embodiment, collagen is the molecule of the ECM that is assayed and the culture of fibroblasts is advantageously maintained for about 48 hours.

According to one embodiment, at confluency, an ingredient of cosmetic and/or pharmaceutical interest is added to the culture medium. It can also be a control ingredient for stimulation or inhibition of molecules of the ECM. Preferably, the stimulation control is selected from vitamin C and TGF beta, advantageously when the cells in culture are fibroblasts. Vitamin C is then used advantageously at a dose in the range from 5 µM to 100 µM, more preferably at 50 µM. TGF beta is then used advantageously at a dose in the range from 1 ng/ml to 100 ng/ml, preferably at 10 ng/ml.

Preferably, the cells are cultured at confluency in the culture medium containing the ingredient of cosmetic and/or pharmaceutical interest for at least 24 hours and preferably up to 6 days, and preferably 24 to 96 hours, preferably for 48 hours.

A step of totally or partially collecting the culture medium is then preferably carried out. According to an advantageous embodiment, the molecule of the ECM under investigation and contained in the culture medium, optionally in a precursor form, is assayed by an immunological method, preferably by an ELISA-type assay.

The method according to the invention then comprises a step of lysis of the cells in culture with a solution of quaternary amine, preferably an aqueous solution, more preferably a solution of ammonium optionally in the form of salts. According to a preferred embodiment, the solution of quaternary amine is selected from an ammonium chloride solution, an ammonium hydroxide solution and mixtures thereof.

According to the invention, "solution of quaternary amine" means a solution in which the quaternary form of the amine represents at least 51% of the amine forms.

According to a preferred embodiment, the solution of quaternary amine contains only the quaternary amine in aqueous solution. According to another preferred embodiment, the solution of quaternary amine has a basic pH, preferably between 10 and 13, more preferably 11.

The results presented in example 3 demonstrate the advantages of the solutions of quaternary amine relative to the conventional solutions for cell lysis. Surprisingly, the solution of quaternary amine in fact presents the best cell lysis rates and the best rates of assay of the molecules of the ECM.

During this lysis step, the solution of quaternary amine is brought into contact with the cells in culture in a state of confluency, and preferably after total or partial removal of the culture medium.

The solution of quaternary amine is applied at a concentration sufficient for cell lysis. Studies done by the applicant demonstrated that a concentration sufficient for cell lysis is generally in the range from 100 μM to 2 M. According to a preferred embodiment, the concentration of the solution of quaternary amine is from 1 mM to 200 mM, more preferably from 10 mM to 100 mM and even more preferably 20 mM. In the particular case when the culture medium has not been removed or only partially, the dilution factor is taken into account for adjusting the concentration of the solution of quaternary amine.

These studies, which are presented partly in examples 2, notably show that the preferred lysis time is between 5 and 60 minutes. Indeed, the results obtained with longer times are not better and do not justify longer lysis times.

According to an advantageous embodiment, the solution of quaternary amine is selected from an ammonium chloride solution at a concentration in the range from 100 μM to 2 M, preferably from 1 mM to 200 mM, preferably 10 mM to 100 mM, preferably at a concentration of 20 mM, and an ammonium hydroxide solution at a concentration in the range from 100 μM to 2 M, preferably from 1 mM to 200 mM, preferably 10 mM to 100 mM, preferably at a concentration of 20 mM and mixtures thereof.

According to an alternative embodiment, the solution of quaternary amine is preferably selected by comparing with the results obtained with ammonium hydroxide solution at 20 mM for 10 minutes and in particular gives, when tested in the same conditions, the same ratio of ECM molecule/DNA at plus or minus 16%, and preferably without significant difference with ammonium hydroxide at 20 mM for 10 minutes.

According to a preferred embodiment, the concentration and time of application of the solution of quaternary amine, preferably of ammonium, are selected by comparing with the results obtained with an ammonium hydroxide lysis solution at 20 mM applied for 10 minutes. Thus, the ratio of the result of the assay of the molecule of the ECM obtained in step e) to the result of the assay of the DNA in the cell lysate is compared with that obtained with an ammonium hydroxide lysis solution at 20 mM applied for the same time.

Preferably, the comparison is carried out by a so-called One Way Anova test of statistical analysis of variances and the concentration and the time of application are selected in such a way that the ratio of the solution tested is not significantly different for at least $p<0.05$ and preferably $p<0.001$.

The lysis step is preferably carried out at room temperature, preferably between 15° C. and 25° C., preferably 20° C. It is preferably carried out with stirring.

The method according to the invention then comprises a step of collecting the cell lysate.

According to an advantageous embodiment, the cell lysate is analysed. According to a preferred embodiment, a step of measurement of the amount of DNA is carried out in order to rationalize the results of assay of the molecules of the ECM by the amount of DNA. This embodiment thus makes it possible to compare the results obtained indirectly rationalized by the number of viable cells in culture. In the case of evaluation of an ingredient of cosmetic and/or pharmaceutical interest in particular, this embodiment thus makes it possible to express the effect observed on the molecule of the ECM, for example a stimulation per cell.

The step of measurement of the amount of DNA in the lysate can be carried by the usual techniques in this field, for example a biochemical assay using an intercalating agent detected by fluorescence.

According to an advantageous embodiment, the molecule of the ECM studied and contained in the cell lysate, optionally in a precursor form, is assayed by an immunological method, preferably by ELISA-type assay.

The method according to the present invention then comprises a step of assay of the molecule contained in the extracellular matrix using an immunological technique, preferably by the TRF fluorescence method.

According to a preferred embodiment, the results of assaying the molecule of the ECM are rationalized by the amount of DNA. The fluorescence measurement can be converted to quantity of molecule of the ECM based on a standard range as is usual in this type of assay.

According to a preferred embodiment, the culture medium collected in step b) and/or the cell lysate collected in step d) are analysed, to advantageously allow the assaying of the molecule of the ECM in the various compartments: intracellular compartment, in the culture medium compartment and in the ECM compartment.

The present invention also relates to a method of in vitro assay method using an immunological technique of at least one molecule of the extracellular matrix synthesized by cells in culture comprising at least the successive steps:
a) a step of culturing the cells,
b) a step of collecting the culture medium and of assaying the molecule of the ECM and/or a precursor of the molecule of the ECM,
c) a step of cell lysis with a solution of quaternary amine,
d) a step of collecting the cell lysate and of assaying the DNA and/or of assaying the molecule of the ECM and/or a precursor of the molecule of the ECM,
e) a step of assaying said molecule of the ECM contained in the extracellular matrix by an immunological technique.

The preferred embodiments were described above. This method advantageously makes it possible to assay the molecule of the ECM in the various compartments: intracellular compartment, in the culture medium compartment and in the ECM compartment.

The present invention also relates to the use of the assay method according to the invention for screening one or more ingredients of cosmetic and/or pharmaceutical interest.

Thus, the present invention also relates to a method of screening and/or of study in vitro of at least one ingredient of cosmetic and/or pharmaceutical interest for its properties of increasing or decreasing the quantity of a molecule of the extracellular matrix. The method of screening and/or of study according to the invention comprises the assay method according to the invention described above in which the cells are cultured in the presence of the ingredient. During step a) the cells at confluency in the culture medium containing the ingredient of cosmetic and/or pharmaceutical interest are cultured for at least 24 hours and preferably for 24 to 96 hours, preferably for 48 hours.

Advantageously, the method of screening and/or of study according to the invention comprises at least the successive steps:
a) a step of culturing the cells, and culturing the cells at confluency for at least 24 hours, in the presence of the ingredient,
b) preferably a step of collecting the culture medium and more preferably of assaying the molecule of the ECM and/or a precursor of the molecule of the ECM in said culture medium thus collected,
c) a step of cell lysis with a solution of quaternary amine,
d) a step of collecting the cell lysate and preferably of assaying the DNA and/or of assaying the molecule of the ECM and/or a precursor of the molecule of the ECM,
e) a step of assaying said molecule of the ECM contained in the extracellular matrix by an immunological technique.

According to a preferred embodiment, the method further comprises a step f) of determination of the properties of the ingredient for increasing or decreasing the quantity of a molecule of the extracellular matrix.

The determination of the capacity, of the ingredient, for stimulation or inhibition is then determined relative to an experiment carried out without ingredient and/or carried out with an ingredient that is a positive control. In the case when collagen is the molecule of the ECM assayed, the positive control is preferably selected from vitamin C at a concentration ranging from 5 µM to 100 µM and preferably at 50 µM, TGF beta preferably at a dose ranging from 1 ng/ml to 100 ng/ml, more preferably at 10 ng/ml and mixtures thereof. Ascorbic acid and TGF beta are indeed so-called collagen "booster" ingredients and investigations carried out by the applicant have demonstrated their advantages in the assay method according to the invention (example 5).

The ingredient is then classified according to the ratio of the assay of the molecule of the ECM in step e) rationalized by the DNA measured in step d) by comparison with the ratio of the assay carried out without ingredient and/or with a positive control rationalized by the DNA measured in step d). The comparison is preferably carried out by a so-called One Way Anova statistical analysis of variances.

- if the ratio obtained with the ingredient is significantly greater than that obtained with the untreated control for at least $p<0.05$ and preferably $p<0.001$, then the ingredient increases the functionality of the molecule in the ECM, i.e. its content in the ECM,
- if the ratio of the ingredient is significantly greater than that obtained with ascorbic acid and/or TGF beta wherein at least $p<0.05$ and preferably $p<0.001$, then the ingredient increases the functionality of collagen in the ECM, i.e. its content in the ECM,
- if the ratio of the ingredient is significantly less than that of the untreated control wherein at least $p<0.05$ and preferably $p<0.001$ then the ingredient decreases the functionality of the molecule in the ECM, i.e. its content in the ECM, An ingredient of cosmetic interest having the capacity to increase the content of molecules of the ECM assayed in the ECM, in particular for collagen, greater than ascorbic acid at 50 µM, can be used for cosmetic care, in particular for anti-ageing treatment, in particular for reducing wrinkles and the signs of cutaneous ageing, and/or for improving the firmness of the skin.

An ingredient of pharmaceutical interest having the capacity to increase the content of molecules of the ECM assayed in the ECM, in particular for collagen, greater than vitamin C at 50 µM, can be used for improving the wound healing process, for the treatment of arthrosis.

An ingredient of pharmaceutical interest having the capacity of decreasing the content of molecules in the ECM can be used for the treatment of fibrosis and of hypertrophic scars.

The present invention further relates to a kit for assay by an immunological method useful for carrying out the assay method according to the invention and/or for the method of screening and/or of study of an ingredient of cosmetic and/or pharmaceutical interest according to the invention, comprising a solution of quaternary amine and an antibody directed against the molecule of the ECM. The preferred and/or advantageous characteristics of the solution of quaternary amine were described above in the context of the method according to the invention.

The antibody directed against the molecule of the ECM is a monoclonal or polyclonal antibody and is preferably selected from an anti-collagen antibody, an anti-elastin antibody and mixtures thereof.

The antibody can be measured, optionally by using a secondary antibody, by enzyme-substrate assay techniques of the EIA (Enzyme Immuno Assay) type, notably ELISA (Enzyme-Linked Immunosorbent Assay), by radiolabelling called RIA (Radioimmunoassay) and by measurement of fluorescence called FIA (Fluorescent immunoassay) in particular by time-delayed fluorescence, called TRF (Time Resolved Fluorescence).

According to a preferred embodiment, the assay kit according to the invention further comprises a solution of ascorbic acid at a preferred concentration in the range from 5 µM to 100 µM and preferably at 50 µM.

According to a preferred embodiment, the assay kit according to the invention also comprises an antibody directed against the precursor of the molecule of the ECM and/or a solution of bisbenzimide for DNA assay according to the method according to the invention.

The present invention also relates to the use of an assay kit according to the invention for implementing the method according to the invention.

The present invention also relates to a method of selecting a lysis solution useful in the assay method according to the invention, wherein the assay method according to the invention is carried out with a lysis solution to be tested for at least 10 min, preferably 10 min, and the ratio of the result of the assay of the molecule of the ECM obtained in step e) to the result of the assay of the DNA in the cell lysate is compared with that obtained with an ammonium hydroxide lysis solution at 20 mM applied for the same time, preferably 10 minutes.

Preferably, the comparison is carried out using a so-called One Way Anova statistical analysis of variances and the lysis solution tested is selected if the ratio of the solution tested is not significantly different for at least $p<0.05$ and preferably $p<0.001$.

The lysis solution thus selected can be used instead of the solution of quaternary amine in the assay method according to the invention. The present invention thus also relates to the lysis solutions selected by the method of selection according to the invention.

According to a preferred embodiment, the methods according to the invention consists of steps a), b), c), d) and e) and optionally f).

Other objectives, features and advantages of the invention will appear clearly to a person skilled in the art after reading the explanatory description which refers to examples which are given solely by way of illustration and do not in any way limit the scope of the invention.

The examples are an integral part of the present invention and any feature that appears novel with respect to any prior art based on the description taken in its entirety, including the examples, is an integral part of the invention both functionally and generally.

Thus, each example has a general scope.

Furthermore, in the examples, and unless indicated otherwise, the temperature is expressed in degrees Celsius, and the pressure is atmospheric pressure, unless indicated otherwise.

EXAMPLES

Example 1

Assay Method for Type I Collagens in the ECM According to the Invention

Principle:

The molecule of the ECM assayed by the method according to the invention is type I collagen synthesized by the fibroblasts.

Protocol:

Step a):

Normal human fibroblasts obtained from abdominal biopsies were seeded in a 96-well plate and cultured in a defined medium (FGM) to 100% confluency, which was obtained after 3 days of culture.

Step b):

After 48 hours of culture post-confluency, the culture medium was removed and discarded.

Step c):

A lysis step was carried out: 110 μl of an ammonium hydroxide solution at 20 mM for 10 minutes at room temperature and with stirring.

Step d):

The lysate was collected and analysed. The double-stranded DNA contained in the lysate was assayed by using the bisbenzimide method (Picogreen Kit, Invitrogen).

Step e):

The collagen in the ECM was assayed directly on the ECM by using an anticollagen I antibody. A secondary antibody conjugated to europium was used with a detection solution and the fluorescence was measured. (Delfia® kit—Perkin Elmer).

The fluorescence results were rationalized relative to the amount of dsDNA measured.

The experiment was carried out on 6 wells (n=6).

The results presented correspond to the mean value (Mean) and the standard deviation (SD)

Results:

| Coll I (RFU) | Mean | 104228 |
| | SD | 4757 |
| DNA (ng/ml) | Mean | 303.01 |
| | SD | 10.98 |
| RATIO Coll I/DNA | Mean | 343.98 |
| | SD | 12.79 |

Discussion:

As the amount of fluorescence is proportional to the measured amount of collagen, the amount of collagen can be determined by using a standard range.

Example 2

Study of the Influence of the Lysis Time on the Assay Method for Type I Collagen in the ECM According to the Invention Principle:

The molecule of the ECM assayed by the method according to the invention is type I collagen synthesized by the fibroblasts as a function of the lysis time.

Protocol:

The protocol described in example 1 was used with different durations of the lysis step with ammonium hydroxide solution 20 mM in the range from 5 minutes to 240 minutes.

The experiment was carried out for each duration in 6 wells (n=6).

The results presented correspond to the mean value (Mean) and the standard deviation (SD) and the significance was determined by One Way Anova analysis (Dunnett) as regards to the optimum duration of 10 minutes.

NS: not significant NT: not analysable

*: significant at $p<0.05$ : significant at $p<0.01$ *: significant at $p<0.001$ Results:

TABLE 2

| Time (min) | | 2'30 | 5 | 7'30 | 10 | 15 | 30 | 60 | 120 |
|---|---|---|---|---|---|---|---|---|---|
| Coll I (RFU) | Mean | 44319 | 46031 | 48762 | 50351 | 49301 | 51632 | 53188 | 52667 |
| | SD | 2416 | 2436 | 1492 | 1377 | 2224 | 3404 | 3830 | 4143 |
| | Dunnett | * | NS | NS | — | NS | NS | NS | NS |
| dsDNA (ng/mL) | Mean | 155.11 | 291.35 | 363.72 | 430.25 | 438.66 | 412.30 | 417.94 | 422.42 |
| | T-test | 26.26 | 46.95 | 15.16 | 39.21 | 28.57 | 15.85 | 15.59 | 17.44 |
| | Dunnett | ** | ** | ** | — | NS | NS | NS | NS |
| Ratio= Coll/ dsDNA | Mean | 295.57 | 161.88 | 134.18 | 117.86 | 112.87 | 125.31 | 127.22 | 124.89 |
| | SD | 70.62 | 30.23 | 4.91 | 11.29 | 10.11 | 8.13 | 7.07 | 11.68 |
| | Dunnett | * | NS | NS | — | NS | NS | NS | NS |

Conclusion:

It is observed that at 2.5 minutes, the DNA extracted is in too small an amount for detecting the quantity of viable cells. Starting from 5 minutes, the amount of collagen measured and the amount of dsDNA are homogeneous over time. The collagen is not degraded by the ammonium hydroxide solution over time and the optimum lysis time is determined at 10 minutes. Experiments with durations of the lysis step of up to 48 hours were carried out and they confirmed these observations.

Example 3

Study of the Influence of the Nature of the Lysis Solution on the Assay Method of Type V Collagen in the ECM According to the Invention Principle:

The molecule of the ECM assayed by the method according to the invention is type V collagen synthesized by the fibroblasts and the study is done according to the nature of the lysis solution.

Protocol:

The protocol described in example 1 was applied in the same way.

Thus, normal human fibroblasts obtained from abdominal biopsies were seeded in a 96-well plate and cultured in a defined medium (FGM) to 100% confluency.

After 48 hours of culture post-confluency at 37° C. under 0.5% $CO_2$, the culture medium was collected.

The lysis solutions tested were as follows:

solution according to the invention $NH_4OH$: 110 μl of an ammonium hydroxide solution at 20 mM.

solution 1: solution containing 52.55 g of urea, 15.01 g of thiourea, 964 mg of DTT and 37.2 mg EDTA solution 2: solution containing Tris 10 mM/Triton 0.1% solution 3: solution containing Hepes 50 mM solution 4: solution containing Tris HCl at 50 Mm (pH7.5), a detergent (deoxycholate sodium at 0.5 mM) and a chelating agent (EGTA at 20 mM)

solution 5: solution containing EDTA 50 mM solution 6: solution containing NaOH 0.2 N and 1% SDS The time of application of the lysis solution tested was 10 minutes at room temperature and with stirring.

The lysate was collected and analysed. The double-stranded DNA contained in the lysate was assayed by using the bisbenzimide method (Picogreen Kit, Invitrogen).

The collagen V in the ECM was assayed directly on the ECM by using an anticollagen V antibody. A secondary antibody conjugated to europium was used with a detection solution and the fluorescence was measured. (Delfia® kit—Perkin Elmer).

The fluorescence was measured.

The experiment was carried out for each lysis solution in 6 wells (n=6).

The results are presented in Table 3.1.

The experiment was repeated and the lysis solutions tested were as follows:

solution according to the invention $NH_4OH$: 110 µl of an ammonium hydroxide solution at concentrations between 200 µM and 2 M.

Solution of monoethylamine at 20 mM

Solution of diethylamine at 20 mM

Solution of triethylamine at 20 mM

The results are presented in Tables 3.2 and 3.3.

The results presented correspond to the mean value (Mean) and the standard deviation (SD) and the significance was determined by One Way Anova analysis (Dunnett) as regards to the $NH_4OH$ lysis solution.

NS: not significant NT: not analysable

*: significant at $p<0.05$ : significant at $p<0.01$ *: significant at $p<0.001$ Results:

TABLE 3.1

| Solution | | $NH_4OH$ | 1 | 2 | 3 | 4 | 6 | 5 |
|---|---|---|---|---|---|---|---|---|
| Coll V | Mean | 60881 | 61017 | 60947 | 50135 | 53508 | 46558 | 13513 |
| (RFU) | SD | 2948 | 3703 | 2166 | 1768 | 3063 | 5972 | 4489 |
| DNA | Mean | 316.27 | 501.08 | 155.80 | 23.50 | 156.22 | 5.80 | 0 |
| | SD | 21.51 | 128.84 | 13.47 | 7.48 | 5.68 | 3.85 | 0.18 |
| Ratio: | Mean | 193.13 | 126.61 | 388.64 | 2342 | 342.76 | 10447 | 0 |
| Coll/DNA | SD | 14.57 | 30.62 | 23.07 | 856 | 21.40 | 5080 | 0 |
| | Anova (Dunnett) | — | ** | ** | NT | ** | NT | NT |

TABLE 3.2

| Solution | | $NH_4OH$ 20 µM | Monoethylamine | Diethylamine | Triethylamine |
|---|---|---|---|---|---|
| Coll V | Mean | 104228 | 67663 | 46155 | 54680 |
| (RFU) | SD | 4757 | 4044 | 1849 | 3176 |
| DNA | Mean | 303.01 | 827.11 | 774.15 | 752.26 |
| | SD | 10.98 | 185.49 | 31.20 | 60.70 |
| Ratio: | Mean | 343.98 | 81.81 | 59.62 | 72.69 |
| Coll/DNA | SD | 12.79 | 20 | 4.31 | 7.16 |
| | % | 100 | 23.78 | 17.33 | 21.13 |
| | Anova (Dunnett) | — | *** | *** | *** |

TABLE 3.3

| Solution | | $NH_4OH$ 200µM | 2 mM | 20 mM | 200 mM | 2M |
|---|---|---|---|---|---|---|
| Coll V | Mean | 114177 | 117380 | 104228 | 118318 | 119292 |
| (RFU) | SD | 5889 | 6187 | 4757 | 6504 | 2839 |
| DNA | Mean | 282.65 | 259.39 | 303.01 | 397.80 | 512.48 |
| | SD | 21.05 | 25.23 | 10.98 | 41.95 | 34.27 |
| Ratio: | Mean | 403.95 | 452.53 | 343.98 | 297.43 | 232.77 |
| Coll/DNA | SD | 41.81 | 77.75 | 12.79 | 41.73 | 17.50 |
| | % | 117.43 | 131.56 | 100.00 | 86.47 | 67.67 |
| | Anova (Dunnett) | ns | ns | — | ns | ns |

Discussion:

The tests carried out demonstrate that ammonium hydroxide solution makes it possible to obtain results that are more reliable, repeatable and reproducible than with the common solutions for cell lysis and solutions of primary, secondary and tertiary amine. Ammonium hydroxide solution permits assays in best conditions both for cell lysis and for the measurement of collagen V. The other solutions of quaternary amine tested also showed very interesting results both for cell lysis and measurement of collagen V. Moreover, the collagen V/DNA ratios obtained with different concentrations of ammonium hydroxide lysis solution are not significantly different from that obtained with a solution at 20 Mm. This solution concentration is optimum owing to its convenience of use.

Example 4

Assay Method for Type I Collagen in the Three Compartments According to the Invention Principle:

The different compartments: intracellular compartment (cell lysate), culture medium compartment and ECM compartment were collected and the different forms of collagen I were assayed.

Protocol:

The method described in example 1 was applied and the culture medium and lysis medium collected were analysed.

The experiment was carried out without active ingredient on the one hand and with ascorbic acid solubilized in PBS at different concentrations from 0.1 to 100 µM.

On the collected culture medium, a procollagen assay was carried out (PIPc kit, TAKARA) by ELISA for determining the amount of extracellular procollagen (Table 4.1)

On the collected lysis medium, a procollagen assay (PIPc kit, TAKARA) by ELISA was carried out for determining the amount of intracellular procollagen (Table 4.2). A DNA assay (Picogreen kit, Invitrogen) was also carried out for rationalizing all of the measurements in each well to the quantity of viable cells.

The amount of collagen I in the ECM was assayed and is presented in Table 4.3.

The amounts of collagen and procollagen measured were rationalized to the amount of DNA present in each well.

A One Way Anova statistical analysis was carried out relative to the control.

NS: not significant NT: not analysable
*: significant at p<0.05 : significant at p<0.01 *: significant at p<0.001

Results:

TABLE 4.1

| Active ingredient | | control | Ascorbic acid (µM) | | | | |
| --- | --- | --- | --- | --- | --- | --- | --- |
| | | | 0.1 | 1 | 10 | 50 | 100 |
| Procoll ng/ml | Mean | 2104 | 1987 | 1983 | 2756 | 2852 | 2845 |
| DNA | Mean | 340 | 318 | 303 | 281 | 279 | 291 |
| Ratio: Procoll/DNA | Mean | 6.22 | 6.26 | 6.57 | 9.83 | 10.25 | 9.78 |
| Stat | Mean | 100.00 | 100.75 | 105.74 | 158.16 | 164.89 | 157.30 |
| | SD | 7.15 | 4.74 | 9.07 | 12.22 | 12.01 | 9.26 |
| | Dunnett | — | ns | ns | ** | ** | ** |

TABLE 4.2

| Active ingredient | | control | Ascorbic acid (µM) | | | | |
| --- | --- | --- | --- | --- | --- | --- | --- |
| | | | 0.1 | 1 | 10 | 50 | 100 |
| Procoll ng/ml | Mean | 117 | 116 | 108 | 114 | 60 | 66 |
| DNA | Mean | 340 | 318 | 303 | 281 | 279 | 291 |
| Ratio: Procoll/DNA | Mean | 0.34 | 0.37 | 0.36 | 0.41 | 0.22 | 0.23 |
| Stat | Mean | 100.00 | 102.85 | 100.76 | 108.02 | 60.83 | 63.69 |
| | SD | 6.05 | 4.84 | 9.80 | 10.65 | 7.74 | 8.83 |
| | Dunnett | — | ns | ns | ns | ** | ** |

TABLE 4.3

| Active ingredient | | control | Ascorbic acid (µM) | | | | |
| --- | --- | --- | --- | --- | --- | --- | --- |
| | | | 0.1 | 1 | 10 | 50 | 100 |
| Coll I | Mean | 75204 | 74156 | 74419 | 78694 | 79146 | 79796 |
| DNA | Mean | 340 | 318 | 303 | 281 | 279 | 291 |
| Ratio: Coll I/DNA | Mean | 221.83 | 233.65 | 246.46 | 280.82 | 284.31 | 273.96 |
| Stat | Mean | 100.00 | 105.33 | 111.10 | 126.59 | 128.17 | 123.50 |
| | SD | 3.92 | 3.61 | 6.19 | 6.82 | 7.86 | 4.72 |
| | Dunnett | — | ns | ** | ** | ** | ** |

Discussion:

The amount of procollagen and of collagen can be calculated by referring to a standard curve of human procollagen and collagen respectively.

Ascorbic acid or vitamin C is known to increase the synthesis and secretion of procollagen in the extracellular medium, as is also shown. These effects of stimulation are also measured with the method according to the invention, including with respect to the content of collagen I in the ECM. This effect is dose-dependent up to 50 μM, where the threshold effect of the molecule is observed. The concentration observed in the intracellular compartment under the effect of vitamin C is less than that observed with the untreated control, since procollagen was secreted in the extracellular medium to a greater extent.

Example 5

Use of the Assay Method of Type I Collagen and of Type V Collagen as a Method of Screening Principle:

Active ingredients of cosmetic interest known to have a stimulating effect on collagen synthesis are tested for their effects on type I collagen in the ECM and then on type V collagen in the ECM.

Protocol:

The experiment was carried out according to the protocol described in example 1 with fibroblasts extracted from a biopsy from a 63-year-old donor.

The active ingredients of cosmetic interest that were tested were:

50 μM ascorbic acid solubilized in a PBS buffer solution was tested at different concentrations from 5 to 100 μM.

a hydrolysate of soya protein described in patent application WO2009121422 and marketed by the applicant under the name Phytokine™ was tested at different concentrations from 0.5 to 2% v/v The cells at confluency were incubated in the presence of the active ingredients for 48 hours at 37° C. under 0.5% $CO_2$ or without active ingredient (control) for 48 hours at 37° C. under 0.5% $CO_2$.

The experiment was carried out for each condition in 6 wells (n=6)—The result presented corresponds to the mean value (Mean) and the standard deviation (SD).

The results obtained for the assay of type I collagen under the effect of Phytokine™ are presented in Table 5.1 and those for the assay of type V collagen in Table 5.2.

The results obtained for the assay of type I collagen under the effect of ascorbic acid are presented in Table 5.3 and those for the assay of type V collagen in Table 5.4.

The significance was calculated by the One Way Anova (Dunnett) test relative to the control.

NS: not significant NT: not analysable

*: significant at $p<0.05$ : significant at $p<0.01$ *: significant at $p<0.001$ Results:

TABLE 5.1

| Active ingredient | | Control | Phytokine ™ (% v/v) | | | | |
| --- | --- | --- | --- | --- | --- | --- | --- |
| | | | 0.5 | 1 | 1.25 | 1.5 | 2 |
| Coll I | Mean | 78857 | 86149 | 81474 | 84256 | 82888 | 85938 |
| (RFU) | SD | 793 | 1496 | 1806 | 3592 | 2868 | 2093 |
| DNA | Mean | 282.67 | 284.89 | 271.07 | 272.17 | 260.96 | 254.26 |
| | SD | 6.8 | 7.0 | 4.8 | 7.6 | 6.9 | 8.0 |
| Ratio: | Mean | 277.54 | 302.06 | 300.42 | 307.51 | 315.94 | 341.07 |
| Coll/DNA | SD | 10.4 | 1.8 | 16.2 | 25.3 | 19.4 | 15.6 |
| Versus | Mean | 100 | 108.84 | 108.25 | 110.80 | 112.98 | 122.89 |
| control | SD | 2.62 | 4.09 | 3.28 | 6.00 | 4.23 | 5.22 |
| | Dunnett | — | * | * | * | * | * |

TABLE 5.2

| Active ingredient | | Control | Phytokine ™ (% v/v) | | | | |
| --- | --- | --- | --- | --- | --- | --- | --- |
| | | | 0.5 | 1 | 1.25 | 1.5 | 2 |
| Coll V | Mean | 13479 | 13483 | 14113 | 14451 | 15452 | 16818 |
| (RFU) | SD | 560 | 1096 | 870 | 593 | 751 | 716 |
| DNA | Mean | 268.68 | 259.81 | 250.56 | 250.72 | 247.90 | 222.37 |
| | SD | 7.9 | 5.2 | 7.7 | 7.7 | 5.5 | 8.6 |
| Ratio: | Mean | 49.9 | 51.86 | 56.29 | 57.80 | 62.38 | 72.52 |
| Coll/DNA | SD | 1.4 | 5.3 | 1.5 | 3.0 | 2.5 | 6.7 |
| Versus | Mean | 100 | 103.92 | 112.80 | 115.84 | 125.01 | 151.34 |
| control | SD | 6.3 | 9.84 | 10.68 | 7.72 | 8.75 | 10.69 |
| | Dunnett | — | NS | NS | * | * | * |

TABLE 5.3

| Active ingredient | | Control | Ascorbic acid (μM) | | | | |
| --- | --- | --- | --- | --- | --- | --- | --- |
| | | | 5 | 10 | 25 | 50 | 100 |
| Coll I | Mean | 52511 | 59802 | 59569 | 59088 | 54454 | 50765 |
| (RFU) | SD | 3160.78 | 3278.42 | 2991.90 | 1412.56 | 5177.36 | 5084.09 |

TABLE 5.3-continued

| | | Ascorbic acid (µM) | | | | | |
|---|---|---|---|---|---|---|---|
| Active ingredient | | Control | 5 | 10 | 25 | 50 | 100 |
| DNA | Mean | 242 | 220 | 249 | 232 | 180 | 204 |
| | SD | 17.34 | 23.70 | 9.28 | 13.62 | 30.42 | 25.35 |
| Ratio: | Mean | 217.51 | 273.40 | 239.53 | 254.84 | 309.87 | 249.31 |
| Coll/ | SD | 12.52 | 14.74 | 7.88 | 13.00 | 66.93 | 9.50 |
| DNA | | | | | | | |
| Versus | Mean | 100.00 | 125.69 | 110.12 | 117.16 | 130.66 | 114.62 |
| control | SD | 5.36 | 7.29 | 3.70 | 6.44 | 10.30 | 4.09 |
| | Dunnett | — | * | * | * | * | * |

TABLE 5.4

| | | Ascorbic acid (µM) | | | | | |
|---|---|---|---|---|---|---|---|
| Active ingredient | | Control | 5 | 10 | 25 | 50 | 100 |
| Coll V | Mean | 12337 | 12644 | 14127 | 16172 | 16230 | 17994 |
| (RFU) | SD | 1103.62 | 734.56 | 1072.20 | 971.01 | 1125.26 | 460.87 |
| DNA | Mean | 241 | 212 | 241 | 236 | 236 | 246 |
| | SD | 11.90 | 12.22 | 8.57 | 3.51 | 6.75 | 5.67 |
| Ratio: | Mean | 51.07 | 59.83 | 58.76 | 68.69 | 68.86 | 73.12 |
| Coll/ | SD | 2.40 | 4.56 | 6.39 | 5.29 | 5.32 | 2.83 |
| DNA | | | | | | | |
| Versus | Mean | 100.00 | 117.16 | 115.06 | 134.49 | 134.82 | 143.17 |
| control | SD | 6.10 | 8.17 | 11.46 | 9.63 | 9.32 | 5.08 |
| | Dunnett | — | * | * | * | * | * |

Discussion:

The results show that Phytokine™ induces stimulation of the synthesis of collagen I and V with a significant dose effect, as well as ascorbic acid. For collagen I assay, the optimum dose for efficacy of ascorbic acid is 50 µM.

Example 6

Use of the Assay Method for Type I Collagen as a Method of Screening

Principle:

Active ingredients of cosmetic interest known to have a stimulating effect on collagen synthesis are tested for their effects on type I collagen in the ECM.

Protocol:

The experiment was carried out according to the protocol described in example 1 with fibroblasts extracted from a biopsy of a 63-year-old donor.

The active ingredients of cosmetic interest that were tested are:

50 µM ascorbic acid solubilized in a PBS buffer solution
vegetable extract tested at 1% (v/v) which was an aqueous extract of *Davilla rugosa* leaves.

The cells at confluency were incubated in the presence of the active ingredients for 48 hours at 37° C. under 0.5% $CO_2$ or without active ingredient (control) for 48 hours at 37° C. under 0.5% $CO_2$ The experiment was carried out for each condition in 6 wells (n=6)—The result presented corresponds to the mean value (Mean) and the standard deviation (SD).

The significance was calculated by the One Way Anova (Dunnett) test.

NS: not significant NT: not analysable
*: significant at p<0.05 : significant at p<0.01 *: significant at p<0.001

Results:

| Active ingredient | | Control | Ascorbic acid (50 µM) | vegetable extract 1% (v/v) |
|---|---|---|---|---|
| Coll I (RFU) | Mean | 153536 | 169132 | 263664 |
| | SD | 9729 | 11038 | 9440 |
| DNA | Mean | 539.4 | 497.4 | 384.6 |
| | SD | 22.1 | 26.4 | 16.5 |
| Ratio: | Mean | 284.86 | 340.49 | 687.29 |
| Coll/DNA | SD | 18.16 | 22.11 | 52.09 |
| Versus control | Mean | 100.00 | 119.53 | 241.27 |
| | SD | 6.38 | 7.76 | 18.29 |
| | Dunnett | — | ** | * |

Discussion:

The results show that ascorbic acid at 50 µM and the vegetable extract tested induce an significant increase in the amount of collagen I in the ECM. The vegetable extract tested is more efficient than ascorbic acid and is therefore an ingredient of cosmetic and/or pharmaceutical interest that can be used notably for the cosmetic treatment of wrinkles and for increasing the firmness of the skin.

Example 7

Study of the Properties of Ingredients Screened with the Method According to the Invention Procollagen Assay in the Culture Medium:

In experiment 6, procollagen was assayed in the culture medium collected in step b) in accordance with the method described in example 4.

The results are presented in Table 7.

TABLE 7

| Active ingredient | | Control | Ascorbic acid (50 μM) | vegetable extract 1% (v/v) |
|---|---|---|---|---|
| Procoll (ng/ml) | Mean | 1175 | 1983 | 624 |
| | SD | 156 | 400 | 18.5 |
| DNA | Mean | 539 | 497.3 | 384.6 |
| | SD | 22 | 26.41 | 16.5 |
| Ratio: | Mean | 2.18 | 4.01 | 1.62 |
| ProColl/DNA | SD | 0.33 | 0.9 | 0.08 |
| Versus control | Mean | 100 | 171.17 | 74.35 |
| | SD | 14.98 | 31.53 | 3.5 |
| | Dunnett | — | *** | NS |

Conclusion:

The vegetable extract does not show an increase in procollagen synthesis in the culture medium but had demonstrated an increase in the amount of collagen I in the matrix.

Immunohistochemical Analysis

Protocol: An Immunohistochemical Analysis was Carried Out According to the Following Protocol:

Normal human fibroblasts obtained from a biopsy were seeded on Lab-Tek 8-well slides at a rate of 40 000 cells/cm$^2$ and cultured in the defined culture medium FGM to 100% confluency. The ingredients evaluated, the 1% v/v vegetable extract or 50 μM ascorbic acid were applied for 72 h.

After 72 h culture post-confluency, the culture medium was removed and immunolabelling was performed. The polyclonal anti-collagen I primary antibody was applied, then after removal of the medium the secondary antibody conjugated to a fluorochrome alexa 488 was added.

The fluorescence was examined under an LSM700 confocal microscope.

Results:

The results measured as a function of the fluorescence are as follows:

| Active ingredient | | Control | Ascorbic acid (50 μM) | vegetable extract 1% (v/v) |
|---|---|---|---|---|
| Area/cells | Mean | 1871.01 | 124238.13 | 217414.26 |
| | SD | 8426.84 | 41013.16 | 47249.63 |
| | % | 100 | 114.96 | 201.18 |

Conclusion:

The visualization study was able to confirm the results obtained with the method according to the invention.

These results demonstrate, moreover, the advantages of screening an ingredient as a function of its properties on the quantity of molecules in the ECM and justify the advantages of the method according to the invention.

The invention claimed is:

1. A method for in vitro assaying at least one molecule of an extracellular matrix (ECM) synthesized by cells in culture using an immunological technique, comprising:
    a) culturing cells in a culture medium,
    b) optionally, collecting the culture medium,
    c) lysing the cells with a solution of quaternary amine to obtain a cell lysate,
    d) collecting the cell lysate, and
    e) assaying said molecule in the extracellular matrix by an immunological technique,
    wherein the cells are maintained in culture at confluency for a time ranging from 24 to 96 hours before step c) is carried out, and
    wherein an assay of DNA and/or an assay of molecule of the ECM is carried out in the cell lysate collected in step d).

2. The method according to claim 1, wherein step b) of collecting the culture medium is carried out.

3. The method according to claim 1, wherein the molecule of the ECM is selected from the group consisting of the proteins constituting the ECM, the glycoproteins constituting the ECM, the glycosaminoglycans constituting the ECM, the proteoglycans constituting the ECM, and the growth factors contained in the ECM.

4. The method according to claim 3, wherein the molecule of the ECM is selected from the group consisting of type I, III, V, VI, XII, XIV, XVI, IV and VII collagens, elastin, tropoelastin, fibrillin 1, lysyl oxidase (LOX), lysyl oxydase like (LOXL), Elastin Binding Protein (EBP), fibulins 3 and 5, Emilin 1 and 2, perlecan, versican, decorin, biglycan, lumican, fibronectin, laminin, hyaluronic acid, and heparan sulfate.

5. The method according to claim 3, wherein the molecule of the ECM is selected from the group consisting of vascular endothelial growth factor (VEGF), phatelet-derived growth factor (PDGF), fibroblast growth factor 2 (FGF-2), fibroblast growth factor 7 (FGF-7), and hepatocyte growth factor (HGF).

6. The method according to claim 1, wherein the cells are stromal cells epithelial cells, or endothelial cells.

7. The method according to claim 6, wherein the cells are fibroblasts and/or keratinocytes and/or adipocytes.

8. The method according to claim 1, wherein an active ingredient of cosmetic and/or pharmaceutical interest is added to the culture medium.

9. The method according to claim 8, wherein the ingredient is selected from the group consisting of vitamin C and transforming growth factor (TGF) beta.

10. The method according to claim 2, wherein the molecule of the ECM and/or a precursor of the molecule of the ECM is assayed by an immunological method in the culture medium collected in step b).

11. The method according to claim 1, wherein the solution of quaternary amine is a solution of ammonium, optionally in form of salts.

12. The method according to claim 1, wherein the solution of quaternary amine is selected from a group consisting of an ammonium chloride solution, an ammonium hydroxide solution, and mixtures thereof.

13. The method according to claim 1, wherein the solution of quaternary amine is at a concentration in the range from 10 mM to 200 mM.

14. The method according to claim 1, wherein the solution of quaternary amine is applied on the cells for a time in the range from 5 to 60 minutes.

15. The method according to claim 1, wherein said immunological technique is a time resolved microscopy (TRF) fluorescence method.

16. A method for in vitro assaying at least one molecule of an ECM synthesized by cells in culture using an immunological technique, comprising:
    a) culturing cells in a culture medium,
    b) collecting the culture medium and of assaying the molecule of the ECM and/or a precursor of the molecule of the ECM,
    c) lysing the cells with a solution of quaternary amine to obtain a cell lysate,
    d) collecting the cell lysate and assaying DNA and/or assaying the molecule of the ECM and/or a precursor of the molecule of the ECM contained in the cell lysate, and e) assaying said molecule of the ECM contained in the extracellular matrix by an immunological technique, wherein the cells are maintained in culture at confluency for a time ranging from 24 to 96 hours before step c) is carried out.

17. A method of screening and/or of study in vitro of at least one ingredient of cosmetic and/or pharmaceutical interest for the properties of said ingredient in increasing or decreasing the quantity of a molecule in the extracellular matrix, comprising:
  a) culturing cells in a culture medium comprising an ingredient of cosmetic and/or pharmaceutical interest,
  b) optionally, collecting the culture medium,
  c) lysing the cells with a solution of quaternary amine to obtain a cell lysate,
  d) collecting the cell lysate and assaying DNA and/or assaying the molecule of the ECM and/or a precursor of the molecule of the ECM contained in the cell lysate, and
  e) assaying said molecule of the ECM contained in the extracellular matrix by an immunological technique,
  wherein the cells in culture are maintained in culture at confluency for a time ranging from 24 to 96 hours before step c) is carried out.

18. A method of selecting a lysis solution useful in the method according to claim 1, comprising:
  i) carrying out the method according to claim 1 with a lysis solution to be tested in step c) for at least 10 min, and calculating the ratio of the result of the assay obtained in step e) to the result of the assay of DNA obtained in step d),
  ii) carrying out the method according to claim 1 with an ammonium hydroxide solution at 20 mM as a lysis solution in step c), and calculating the ratio of the result of the assay obtained in step e) to the result of the assay of DNA obtained in step d), and
  iii) comparing the ratio obtained in step i) with the ratio obtained in step ii) to select a lysis solution useful in the method according to claim 1.

19. The method according to claim 16, wherein the solution of quaternary amine is selected from the group consisting of an ammonium chloride solution, an ammonium hydroxide solution, and mixtures thereof, and wherein the solution of quaternary amine is applied on the cells for a time in the range from 5 to 60 minutes at a concentration in the range from 10 mM to 200 mM.

20. The method according to claim 17, wherein step b) of collecting the culture medium is carried out.

21. The method according to claim 19, wherein the molecule of the ECM and/or a precursor of the molecule of the ECM is assayed by an immunological method in the culture medium collected in step b).

22. The method according to claim 17, wherein the solution of quaternary amine is selected from the group consisting of an ammonium chloride solution, an ammonium hydroxide solution, and mixtures thereof, and wherein the solution of quaternary amine is applied on the cells for a time in the range from 5 to 60 minutes at a concentration in the range from 10 mM to 200 mM.

\* \* \* \* \*